United States Patent
Borne et al.

(10) Patent No.: US 7,607,341 B2
(45) Date of Patent: Oct. 27, 2009

(54) DEVICE FOR MEASURING THE DENSITY OF PARTICLES BY FLOTATION

(75) Inventors: Lionel Borne, Saint-Louis (FR); Jean-Louis Patedoye, Saint-Louis (FR)

(73) Assignee: Institut Franco Allemand de Recherches de Saint-Louis, Saint-Louis (FR)

( * ) Notice: Subject to any disclaimer, the term of this patent is extended or adjusted under 35 U.S.C. 154(b) by 0 days.

(21) Appl. No.: 11/730,902

(22) Filed: Apr. 4, 2007

(65) Prior Publication Data
US 2008/0011079 A1   Jan. 17, 2008

(30) Foreign Application Priority Data
Apr. 13, 2006   (FR) .................... 06 03261

(51) Int. Cl.
*G01N 9/02* (2006.01)
(52) U.S. Cl. ............................ 73/32 R
(58) Field of Classification Search .......... 73/32 R, 73/433–454
See application file for complete search history.

(56) References Cited

U.S. PATENT DOCUMENTS

| | | | | |
|---|---|---|---|---|
| 1,344,370 A * | 6/1920 | Allen | ............ | 210/85 |
| 1,730,221 A | 10/1929 | Larose | | |
| 2,825,698 A | 3/1958 | Taylor et al. | | |
| 3,244,010 A * | 4/1966 | Martin | ............ | 73/437 |
| 3,514,996 A * | 6/1970 | Coustau | ............ | 73/152.04 |
| 3,616,925 A * | 11/1971 | Tolman | ............ | 210/311 |
| 3,661,015 A | 5/1972 | Paul | | |
| 4,290,300 A * | 9/1981 | Carver | ............ | 73/32 R |
| 4,391,141 A * | 7/1983 | Petersen | ............ | 73/433 |
| 6,866,778 B2 * | 3/2005 | Kerschenmeyer et al. | ... | 210/305 |

FOREIGN PATENT DOCUMENTS

DE    820 981        7/1949
SU    1631359 A2     2/1989

OTHER PUBLICATIONS

A.R. Lang, "Dilatation, density and nitrogen content in type 1a diamonds: previous work and proposed experiments," Journal of Physics D: Applied Physics, Dec. 12, 1993, pp. 2239-2244 (XP000421207).

* cited by examiner

*Primary Examiner*—Hezron Williams
*Assistant Examiner*—Gunnar J Gissel
(74) *Attorney, Agent, or Firm*—Oliff & Berridge, PLC

(57) ABSTRACT

The present invention relates to the investigation of particle characteristics, particularly to a device for measuring the apparent density distribution of a set of particles composed of several subsets of particles with different apparent densities and able to implement a flotation process to measure this distribution and comprising a flotation container, a stirrer and a system for measuring the density of the liquids, characterized in that the inside wall of the container has at least a first part in the shape of an inverted cone with axis Y whose height is 1.5 to 3 times its maximum diameter, and in that it has means for extracting liquid communicating with said first part at the vertex of the inverted cone, said means having a tube communicating with said first part at the tip of the inverted cone of which the first axis makes an angle of between $\pi/2$ and $3\pi/2$ radians with the second axis.

15 Claims, 2 Drawing Sheets

DEVICE FOR MEASURING THE DENSITY OF PARTICLES BY FLOTATION

BACKGROUND

The present invention relates to the investigation of particle characteristics, particularly the distribution of these characteristics over a set of particles, and relates in particular to a device for measuring the apparent density distribution of a set of particles that can implement a flotation process.

The creation and practical use of particulate materials are the first steps in manufacturing numerous composite materials. The simplest of these materials are comprised of two components: the particles, and a binder. The application properties of these materials often depend on the microstructure of the elementary particles employed.

Devices are known for measuring the density of a liquid using particles with a known density such as the device described in patent DE820981.

Devices are also known for measuring the density of a mixture of liquid and solid particles such as that described in U.S. Pat. No. 1,344,370. However, these devices do not measure particle density.

The apparent density of the particles can be an important microstructure parameter. For example, it enables the homogeneity of the particles to be characterized quantitatively and their degree of purity or fault density to be determined. The distribution of the apparent density of a set of particles enables the homogeneity of the particle set to be characterized.

The apparent density of a particle is determined by the ratio between its mass and its apparent volume. There are two major groups of methods for measuring particle density: indirect methods and direct methods.

The indirect methods are based on measuring the mass and volume of the particles. They are gas or liquid pycnometer methods. The masses are determined by weighing. The volumes are determined by pressure measurements (gas) or weighing (liquid). These methods give access to the average density of the set of particles. However they do not enable the distribution of the apparent densities over a set of particles to be determined.

The direct methods are based on decanting, also called flotation, within a liquid whose density is being measured. These methods separate the particles denser than the liquid in the lower part from the particles less dense than the liquid in the upper part. Two techniques are used: the density gradient method and the flotation method.

The density gradient method, implemented in particular in U.S. Pat. No. 4,290,300, consists of creating a density gradient in a liquid column. The particles are then released at the top of the column. They descend in the column until the density of the liquid balances the density of the particle. Prior calibration of the column enables the liquid density and column height to be linked. When the stabilization height of each particle is recorded, the apparent density distribution of the particles of a given set can be obtained.

The flotation method consists simply of submerging a particle sample in a liquid of known density, decanting the particles that are denser than the liquid, and collecting and weighing these particles. The principle of this measurement is simple but implementation for an accurate and reproducible result is more delicate. The difficulties of this type of method are the accuracy of monitoring the density of the flotation liquid and extracting fractions of particles deposited at the lower part of the container.

The particle density measuring devices known to date using a flotation separation method involve several major disadvantages, namely separation of the different classes of particles with different densities is not distinct, and recovery of the particles produces recirculation of the flotation liquid, which interferes with extraction and hence with measurement unless additional techniques are used such as the pressure exerted by a fluid on the flotation liquid or centrifugation—techniques that are hazardous if applied to particles of an explosive material.

Centrifugation measuring devices are also known; however, their use involves safety problems in the case of particles of high-energy materials.

SUMMARY

The goal of the invention is to propose a device for measuring the density distribution of a set of particles that can implement a flotation process enabling this density to be determined with high accuracy and presenting no problems of particle extraction or explosion hazard.

The solution provided is a device for measuring the apparent density distribution of a set of particles composed of several subsets of particles with different apparent densities and able to implement a flotation process to measure this distribution. The device includes a flotation container, a stirrer, and a system for measuring the density of the liquids. The inside wall of the container has at least a first part in the shape of an inverted cone with axis Y whose height is 1.5 to 3 times its maximum diameter, and in that it has means for extracting liquid communicating with said first part at the vertex of the inverted cone, said means having a tube communicating with said first part at the tip of the inverted cone whose X axis makes an angle of $2\pi/3 \pm \pi/36$ radians with the Y axis.

"Cone" is to be understood as a geometric shape delimited by said first part of the inside wall. The combination of a cone shape whose height is between 1.5 and 3 times its maximum diameter and an extraction tube whose axis makes an angle of $2\pi/3 \pm \pi/36$ radians allows clean separation of the particles when they are decanted and allows these particles to be recovered without recirculating the flotation liquid and hence without interfering with the measurement.

According to one particular feature, said extraction means comprise a tube connecting the inside of the container to the outside of the container and communicating with the inside of the container at the tip of the cone.

According to one particular feature, said first part is in the shape of a truncated cone, the truncation forming an aperture that communicates with said tube.

According to one particular feature, favoring deposition of the particles on the bottom of the container, the height of the first part is between 1.5 and 3 times its diameter.

According to another particular feature, the X axis of the tube makes an angle of between $\pi/2$ and $\pi$ radians with the Y axis of said cone.

According to one particular feature, the inside wall has a second part of tubular shape surmounting said first part and having the same section as the base of the cone.

According to an additional feature, the inside of the container is connected to a densimeter having a sampling tube that has a filter at its end located inside the container.

According to another feature that improves the accuracy of the results, the container has two walls, an inside wall and an outside wall, the outside wall having apertures connected to a device for regulating the inside temperature of the space separating said inside and outside walls, said means being preferably able to ensure circulation of a liquid at a constant regulated temperature inside said space.

According to one particular feature, the container is closed, on the side opposite that of the extraction means by a lid, preferably made, at least in part, of a heat-insulating material.

According to one particular feature, this lid has at least three bores.

According to one particular feature, the inside part of the container communicates with means able to supply a liquid, these means being preferably able to pass, in part, through one of said bores provided in lid.

According to an additional feature, the outside wall of the container is covered, at least in part, by an insulating material.

According to one particular feature, the device has means for stirring the fluid that, at least in part, are disposed inside the container.

According to another feature, the container is filled with a mixture of at least two liquids, and adjustment of the relative proportions of the two liquids enables the density of the mixture to be finely adjusted. For RDX or HMX particles, it is preferable to use a mixture of toluene and methylene iodide ($CH_2I_2$).

According to an additional feature, the means for supplying the interior of the container with a liquid are able to supply it with toluene.

The invention also relates to a method for measuring the apparent density distribution of a set of particles composed of n subsets of particles with different apparent densities and able to implement a flotation process to measure this distribution using a device as described herein having the following steps:

in a first step, introducing a first flotation liquid and particles to be characterized into the flotation container;
in a second step, homogenizing the mixture so obtained by stirring;
in a third step, allowing the mixture to decant;
in a fourth step, extracting the decanted particles with the aid of the extraction means;
a fifth step, adding a liquid with a lower density than that of the first flotation liquid;
in a sixth, repeating the second, third, fourth, and fifth steps n−1 times.

BRIEF DESCRIPTION OF THE DRAWINGS

Other advantages and characteristics will appear from the description of an embodiment of the invention referring to the attached drawings.

DETAILED DESCRIPTION OF EMBODIMENTS

Figure 1:
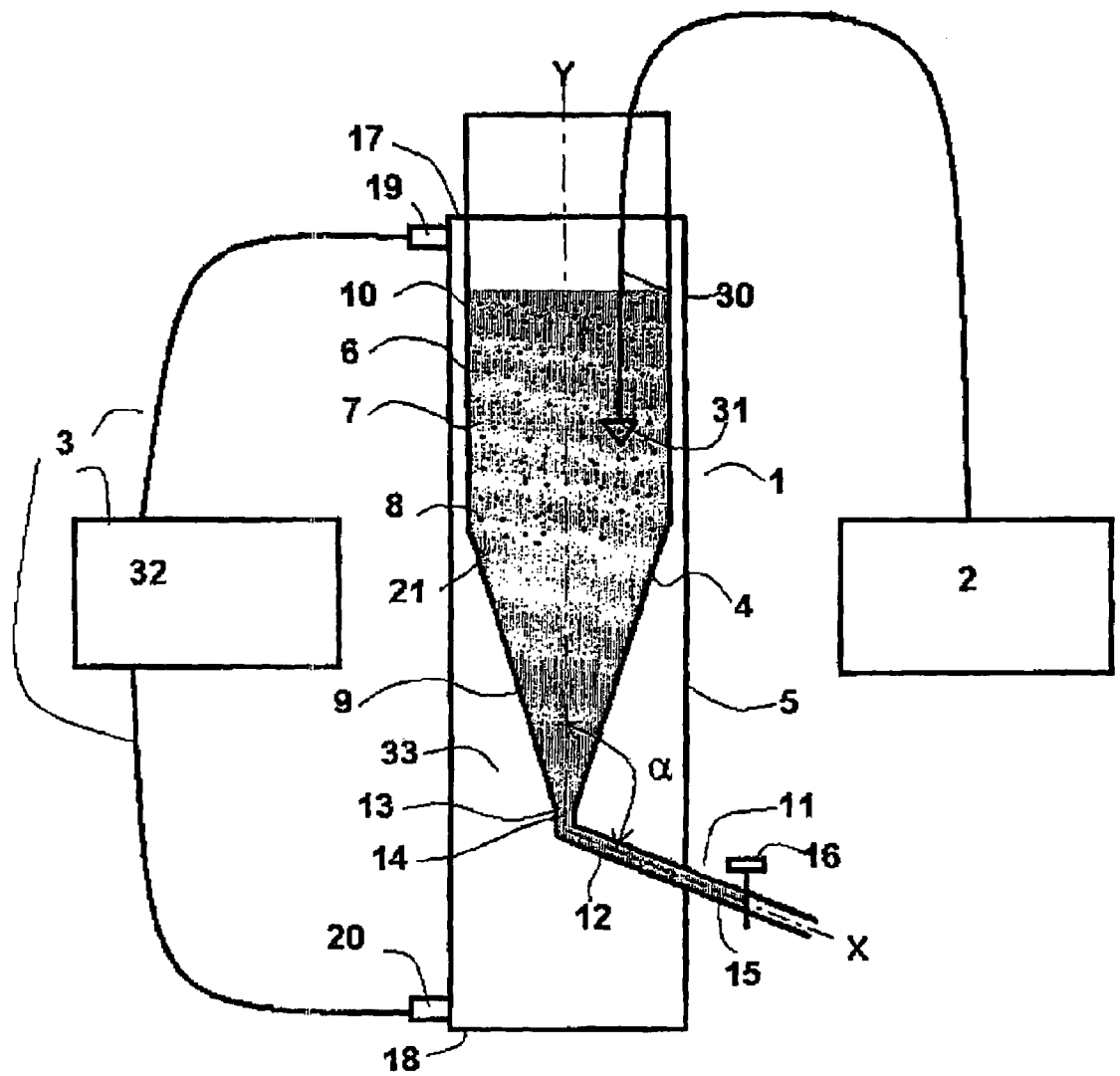
FIG. 1 is a simplified diagram of a device for measuring particle density according to one embodiment of the invention.

As shown in FIG. 1, a device for measuring particle density according to the presented embodiment of the invention is composed of three main parts: a flotation container 1, a system 2 for measuring liquid density, and a temperature regulation system 3.

The flotation container 1 is a double-walled glass container, namely with an inside wall 4 and an outside wall 5. Its inside part 6 contains a flotation liquid 7 in which the particles 8 whose density is to be determined are dispersed. This flotation liquid 7 is comprised of a mixture of toluene and methylene iodide, for example.

Inside wall 4 has a first part 9 in the shape of an inverted truncated cone, a second part 10 of cylindrical tubular shape with the same diameter as the base 21 of the cone delimited by the first part, and a third part 11 composed of a cylindrical tube 12 communicating by one of its ends with the vertex of the cone delimited by the first part 9 of the inside wall 4. Said second part 10 has a diameter of 100 mm and a height of 200 mm. It provides good dispersion of the particles in the flotation liquid 7 with an optimized concentration of particles 8.

Said first part 9, conical in shape, has a height of 200 mm. It enables the particles to be collected when decanted and extracted from the container without creating movements in the fluid that would interfere with measurement.

This first part 9 of the inside wall 4 has, at the vertex 14 of said cone, an aperture 13 that gives it its truncated shape. This aperture communicates with the cylindrical tube 12 with diameter 12 mm whose X axis makes an angle $\alpha$ of between $\pi/2$ and $3\pi/2$ radians, preferably in the range $2\pi/3 \pm \pi/36$ with the Y axis.

This cylindrical tube 12, constituting the third part 11 of the inside wall 4, passes through the outside wall 5 of the container and, at its part 15 located outside container 1, has a valve 16 by which the emptying rate of the container can be adjusted. Tube 12 and the valve 16 are means of extracting the flotation liquid.

The outside wall 5 of container 1 has a cylindrical tubular shape and is joined to the inside wall 4 at its upper end 17; it is closed at its lower end 18. This outside wall also has two apertures, an aperture 19 at its upper end 17 and an aperture 20 at its lower end 18, these apertures 19 and 20 being intended for connection to the temperature regulation system 3.

Figure 2:
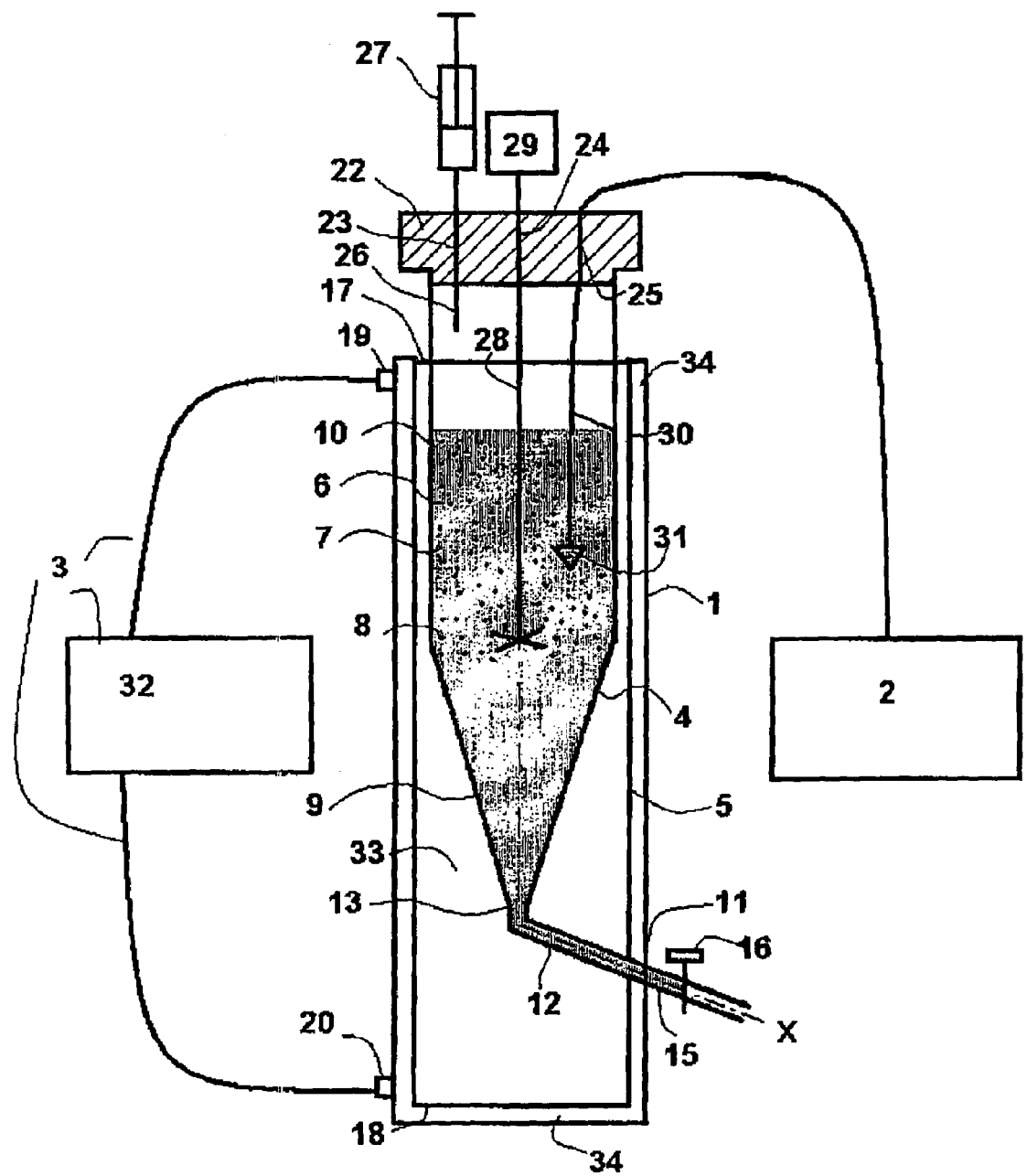
FIG. 2 is a complete drawing of a device for measuring particle density according to this embodiment of the invention.

As shown in FIG. 2, the flotation container 1 is provided with a lid 22 that ensures density stability of the flotation mixture 7 by preventing any preferred evaporation of one of the liquids in this flotation mixture, and limits heat losses from the liquid 7. This lid has three bores 23, 24, and 25 that, respectively, enable passage of:

End 26 of a syringe 27 that adjusts the density of the flotation mixture by adding one of its components;

A part 28 of a screw stirrer 29 that provides intimate mixing and good homogeneity of the flotation mixture. Density gradients in the container must be avoided;

A tube 30 for sampling the flotation liquid to measure the density of the flotation mixture. This tube has a filter 31 at its end located inside the container. This filter 31 can allow liquid to pass through, but not the particles 8. It was manufactured and placed at the end of sampling tube 30 in liquid 7 in the internal part 6 of flotation container 1 in order not to aspirate particles 8 when sampled and interfere with density measurement. It is frustroconical and made of brass. The vertex of the cone has a diameter of 5 mm and is connected by the sampling tube to the densimeter. The cone height is 30 mm. An 80 μm square-mesh screen is crimped to the base of the cone. The cone base diameter is 17 mm.

The liquid density measuring system is an "A. Paar" digital densimeter of the DMA 48 type. This densimeter measures the density of a liquid using the vibrating tube principle. As the sample temperature is controlled precisely (0.1° C.), the liquid density measurement accuracy is ±0.0001 g/cm$^3$. The sensitivity of the experimental device is 0.00003 g/cm$^3$. The optional system (Fill Rinse System) for an automatic sampling of the flotation mixture in the DMA 48 is employed.

The temperature regulation system 3 is a water circulation device. It is a commercial cryothermostat 32 of the ministat type. The temperature control accuracy is ±0.1° C.

Water circulation from the cryothermostat passing into space 33 delimited by the inside wall 4 and outside wall 5 of the container, then returning to the cryothermostat, ensures regulation of the temperature of the flotation liquid 7. To minimize the influence of the outside temperature, the flotation container 1 is placed in a sheath 34 of heat-insulating foam.

The entire experimental device is preferably placed in a room whose temperature is lower than the temperature of the flotation liquid. If the temperature of the flotation liquid is regulated at 20° C., it is desirable for the room temperature to be regulated at about 19° C. This prevents thermal convection currents that could be generated near the drainage valve due to lower heat insulation. These convection currents interfere with particle decanting. This is an important point. This outside temperature control creates a small liquid buffer with a higher density which contains no particles. It enables the valve to be rinsed if needed when particles are collected, and increases measurement accuracy.

This device enables the apparent density distribution of a set of particles to be measured. It provides precise measurement of the apparent density of a particle, but also the distribution of the apparent particle densities within a given set. Moreover, this device enables subsets that have more-homogenous apparent density distributions than that of the initial set, to be extracted from the initial set. Measurement of other characteristics for each of these subsets enables the apparent density measurements to be distributed according to other characteristics, for example particle size.

The operating method described below relates to a process for measuring the apparent density of hexogen (RDX) or octogen (HMX) particles implemented with a device according to the invention.

This device enables the apparent density distribution of a set of particles to be measured. It provides precise measurement of the apparent density of a particle, but also the distribution of the apparent particle densities within a given set. Moreover, this device enables subsets that have more-homogenous apparent density distributions than that of the initial set, to be extracted from the initial set. Measurement of other characteristics for each of these subsets enables the apparent density measurements to be distributed according to other characteristics, for example particle size.

The container is filled with 1.5 liters of flotation liquid. The choice of this liquid or mixture of liquids is based on two main requirements:
  The possibility of finely adjusting its density by varying its composition, for example;
  Good wettability properties with respect to the particles to be characterized.

The flotation liquid must have no effect on the particles. If the particles have poor solubility in this liquid, the precaution must be taken of working with a liquid saturated with the material of which the particles are composed.

In this embodiment, the flotation liquid 7 is comprised of a mixture of toluene and methylene iodide.

A particle mass is introduced into the flotation mixture. This mass is determined according to the nature of the particles. A number of particles large enough to be statistically representative of the set studied is required. However, the concentration of the particles in the liquid must be limited to avoid interactions between the particles when decanted. In this embodiment, the mass of RDX particles is between 30 and 40 grams.

The particles in the flotation mixture within the sealed container are dispersed by mechanical stirring. This stirring of the flotation mixture ensures its homogeneity. Adjustment of the liquid density is done with the digital densimeter. The various liquid samples, removed from the container by the digital densimeter, are stored in a small attached bottle in order not to interfere with the process of adjusting the sample density.

After verification of the stability of the flotation liquid density, stirring of the system is stopped to allow particles to be decanted. The time necessary to obtain separation between the particles varies according to the size of the particles. It can range between 3 and 10 hours. In all cases, distinct particle separation must be observed.

The particles are then extracted from the container by tube 12, after valve 16 has been opened, and collected on a filter of the sintered glass type and washed with ethanol by aspiration under vacuum. They are then weighed precisely.

Starting from a flotation mixture with a density such that no particle is deposited at the lower part of the container, one proceeds in successive steps, successively lowering the density of the mixture by adding small volumes of toluene and extracting the particles at each step. Injection of about 5 ml of toluene reduces the density of the flotation mixture by about 0.003 $g/cm^3$. This density centers around 1.8 $g/cm^3$ in the case of RDX particles and 1.9 $g/cm^3$ in the case of HMX particles.

The invention claimed is:

1. Device for measuring the apparent density distribution of a set of particles composed of several subsets of particles with different apparent densities and able to implement a flotation process to measure this distribution, comprising:
  a double-walled container having an inside and an outside wall defining an inner and outer chamber;
  a stirrer placed in the inner chamber; and
  a system for measuring a density of the liquids,
  wherein the inside wall of the container includes at least a first part in a shape of an inverted cone with a second axis whose height is 1.5 to 3 times a maximum diameter of the inverted cone, and
  the first part has extraction means for extracting liquid communicating with the first part at a vertex of the inverted cone, the extraction means having a tube communicating with the first part at the tip of the inverted cone of which a first axis makes an angle of between $\pi/2$ and $3\pi/2$ radians with the second axis.

2. Device according to claim 1, wherein the stirrer is placed in the upper part of the inner chamber.

3. Device according to claim 1, wherein the inside wall includes a second part of tubular shape surmounting the first part and having the same cross-section as a base of the cone.

4. Device according to claim 1, wherein a densimeter is connected to an inside part of the container by a sampling tube having a filter at a free end of the sampling tube.

5. Device according to claim 1, wherein the container has two walls, the inside wall and an outside wall, the outside wall having at least two apertures connected to means for regulating the inside temperature of a space separating the inside and outside walls.

6. Device according to claim 5, wherein the regulation means circulates a liquid at a constant regulated temperature inside the space.

7. Device according to claim 1, wherein the container is closed on a side opposite that of the extracting means by a lid.

8. Device according to claim 7, wherein the lid has at least three bores that penetrate the lid from top to bottom.

9. Device according to claim 7, wherein the lid is made at least in part of a heating-insulating material.

10. Device according to claim 1, wherein an inside part of the container communicates with means for supplying a liquid.

11. Device according to claim 10, wherein the resupplying means passes at least in part through one of the bores provided in the lid.

12. Device according to claim 1, wherein an outside wall of the container is covered, at least in part, by an insulating material.

13. Device according to claim 1, wherein the container is filled, at least in part, with a liquid mixture of toluene and methylene iodide.

14. Method for measuring the apparent density distribution of a set of particles composed of n subsets of particles with different apparent densities and able to implement a flotation process to measure this distribution using a device according to claim 1, the method comprising:
- introducing a first flotation liquid and particles to be characterized into a flotation to form a mixture;
- homogenizing the mixture by stirring;
- allowing the mixture to decant; and
- extracting decanted particles with the aid of an extraction means.

15. The method of claim 14, further comprising adding a liquid with a lower density that that of the first flotation liquid and repeating the homogenizing, allowing, extracting, and adding steps are repeated n−1 times.

* * * * *